United States Patent [19]

Sumikawa et al.

[11] Patent Number: 5,463,116
[45] Date of Patent: Oct. 31, 1995

[54] CRYSTALS OF N-(TRANS-4-ISOPROPYLCYCLO-HEXLYCARBONYL)-D-PHENYLALANINE AND METHODS FOR PREPARING THEM

[75] Inventors: Michito Sumikawa; Yoshihito Koguchi; Takao Ohgane; Yasuo Irie, all of Kawasaki; Satoji Takahashi, Yottukaichi, all of Japan

[73] Assignee: Ajinomoto Co., Inc., Tokyo, Japan

[21] Appl. No.: 190,460

[22] Filed: Feb. 2, 1994

Related U.S. Application Data

[63] Continuation-in-part of Ser. No. 166,144, Dec. 14, 1993, which is a continuation of Ser. No. 921,224, Jul. 29, 1992, abandoned.

[30] Foreign Application Priority Data

Jul. 30, 1991 [JP] Japan .................................. 3-189696
Aug. 8, 1991 [JP] Japan .................................. 3-199453

[51] Int. Cl.⁶ .................................................. C07C 229/00
[52] U.S. Cl. ............................ 562/450; 562/444; 562/445
[58] Field of Search ............................ 562/450, 444, 562/445

[56] References Cited

U.S. PATENT DOCUMENTS 4,650,785  3/1987  Toyoshima et al. .................... 562/449
4,670,584  6/1987  Toyoshima et al. .................... 514/3
4,816,484  3/1989  Toyoshima et al. .................... 514/563

OTHER PUBLICATIONS

Yusuke Sato, Masahiko Nishikawa, Hisashi Shinkai and Eiji Sukegawa, *Diabetes Research and Clinical Practice,* vol. 12 (1991) "Possibility of ideal blood glucose by a new oral hyopglycemic agent, N-[(trans-4-isopropycyclohexyl)-carbonyl]-D-phenylalanine (A-4166), and its stimulatory effect on insulin secretion in animals" pp. 53–59.

*Primary Examiner*—Raymond Henley, III
*Assistant Examiner*—Keith MacMillan
*Attorney, Agent, or Firm*—Oblon, Spivak, McClelland, Maier, & Neustadt

[57] ABSTRACT

Stable crystals of N-(trans-4-isopropylcyclohexylcarbonyl)-D-phenylalanine may be produced by treating this compound with a solvent at a temperature of at least 10° C. and forming crystals in the solvent at a temperature of at least 10° C. For example, crystals may be formed by crystallization out of solution, or may be formed from solid particles of the compound suspended in a solvent. Crystals formed in this way have different melting point, infra red spectrum and X-ray diffraction patterns from previously known forms of the compound and have enhanced processability, e.g., stability to grinding.

19 Claims, 5 Drawing Sheets

CRYSTALS OF N-(TRANS-4-ISOPROPYLCYCLO-HEXLYCARBONYL)-D-PHENYLALANINE AND METHODS FOR PREPARING THEM

CROSS REFERENCE TO RELATED APPLICATION

This application is a continuation-in-part of application Ser. No. 08/166,144 filed Dec. 14, 1993 which is a continuation of abandoned application Ser. No. 07/921,224 filed Jul. 29, 1992.

BACKGROUND OF THE INVENTION

The present invention relates to a crystalline form of N-(trans-4-isopropylcyclohexylcarbonyl)-D-phenylalanine and to methods for the production of that crystalline form.

N-(trans-4-isopropylcyclohexylcarbonyl)-D-phenylalanine of formula (1) is a known substance having therapeutic utility in depressing blood glucose levels.

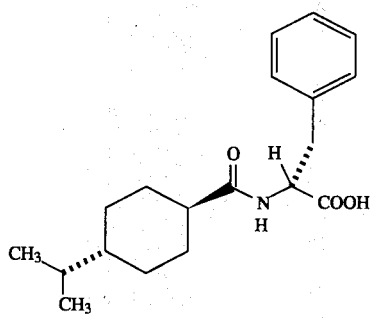

N-(trans-4-isopropylcyclohexylcarbonyl)-D-phenylalanine is disclosed in Japanese Patent Application Laid Open No. 63-54321 (equivalent to EP-A-196222 and US 4,816, 484) and in J. Med. Chem. 32, 1436. The Japanese application describes how the compound may be crystallized from aqueous methanol to yield crystals having a melting point of 129° to 130° C. These crystals are in a crystalline form referred to herein as "B-type". The X-ray powder diffraction pattern and infra-red spectrum of B type crystals are shown in FIGS. 1 and 2 respectively.

The known B-type crystals suffer from problems of instability, especially when subjected to mechanical grinding. The instability results, for example, in conversion of the B-type crystals into other forms. The instability of the B-type crystals means that they are not ideal for use in medicine. It is in general desirable that a medicinal product containing a crystalline active ingredient have a composition which is well defined and stable in terms of the crystalline form of the active ingredient. Conversion of one crystalline form into unknown amounts of different, or amorphous, forms during processing or storage is undesirable and in many cases would be regarded as analogous to the appearance of unquantified amounts of impurities in the product.

The present inventors have discovered a method for producing a crystalline form of N-(trans-4-isopropylcyclohexylcarbonyl)-D-phenylalanine having improved stability over the known B-type. For instance, the crystals according to one aspect of the present invention have enhanced stability to grinding. Such crystals are therefore more suitable for use in medicines than those of the B-type. The crystals having enhanced stability have been designated "H-type" by the inventors.

SUMMARY OF THE INVENTION

According to a first aspect of the invention there is provided a method for the production of N-(trans-4-isopropylcyclohexylcarbonyl)D-phenylalanine comprising treating N-(trans-4-isopropylcyclohexylcarbonyl)-D-phenylalanine with a solvent at a temperature of at least 10° C. and forming said crystals in said solvent at a temperature of at least 10° C.

In one embodiment of this method N-(trans-4-isopropylcyclohexylcarbonyl)-D-phenylalanine is dissolved in the solvent at a temperature of at least 10° C. to form a solution and crystals are then crystallized from the solution at a temperature of at least 10° C.

Alternatively, N-(trans-4-isopropylcyclohexylcarbonyl)-D-phenylalanine is combined at a temperature of at least 10° C. with a solvent in which it is incompletely soluble at that temperature, to form a suspension of solid N-(trans-4-isopropylcyclohexylcarbonyl)-D-phenylalanine, and said suspension is maintained at a temperature of at least 10° C.

According to a second aspect of the invention there are provided crystals of N-(trans-4-isopropylcyclohexylcarbonyl)-D-phenylalanine as obtainable by the method of the first aspect.

According to a still further aspect crystals of N-(trans-4-isopropylcyclohexylcarbonyl)-D-phenylalanine are provided which have at least one, and preferably all, of the following properties:

(a) a melting point in the range of 136° to 142° C.;

(b) an X-ray diffraction pattern having maxima at approximately 2θ=8.1, 13.1, 19.6 and 19.9°; and (c) an infra red spectrum having absorptions at about 1714, 1649, 1542 and 1214 cm$^{-1}$. Such crystals are designated "H-type" herein.

Crystals of the second aspect of the invention desirably comprise enhanced amounts of H-type crystals relative to the starting N-(trans-4-isopropylcyclohexylcarbonyl)-D-phenylalanine.

DESCRIPTION OF THE PREFERRED EMBODIMENTS

As was indicated above one aspect of the present invention provides N-(trans-4-isopropylcyclohexylcarbonyl)-D-phenylalanine in H-type crystalline form. Examples of the physical properties of the H-type crystals are as follows.

The inventors have measured the melting point of H-type crystals and found it to be in the range of 136° to 142°. By contrast, when the melting point of B-type crystals was measured by the same technique a melting point of 128° to 131° C. was found.

Figure 1:
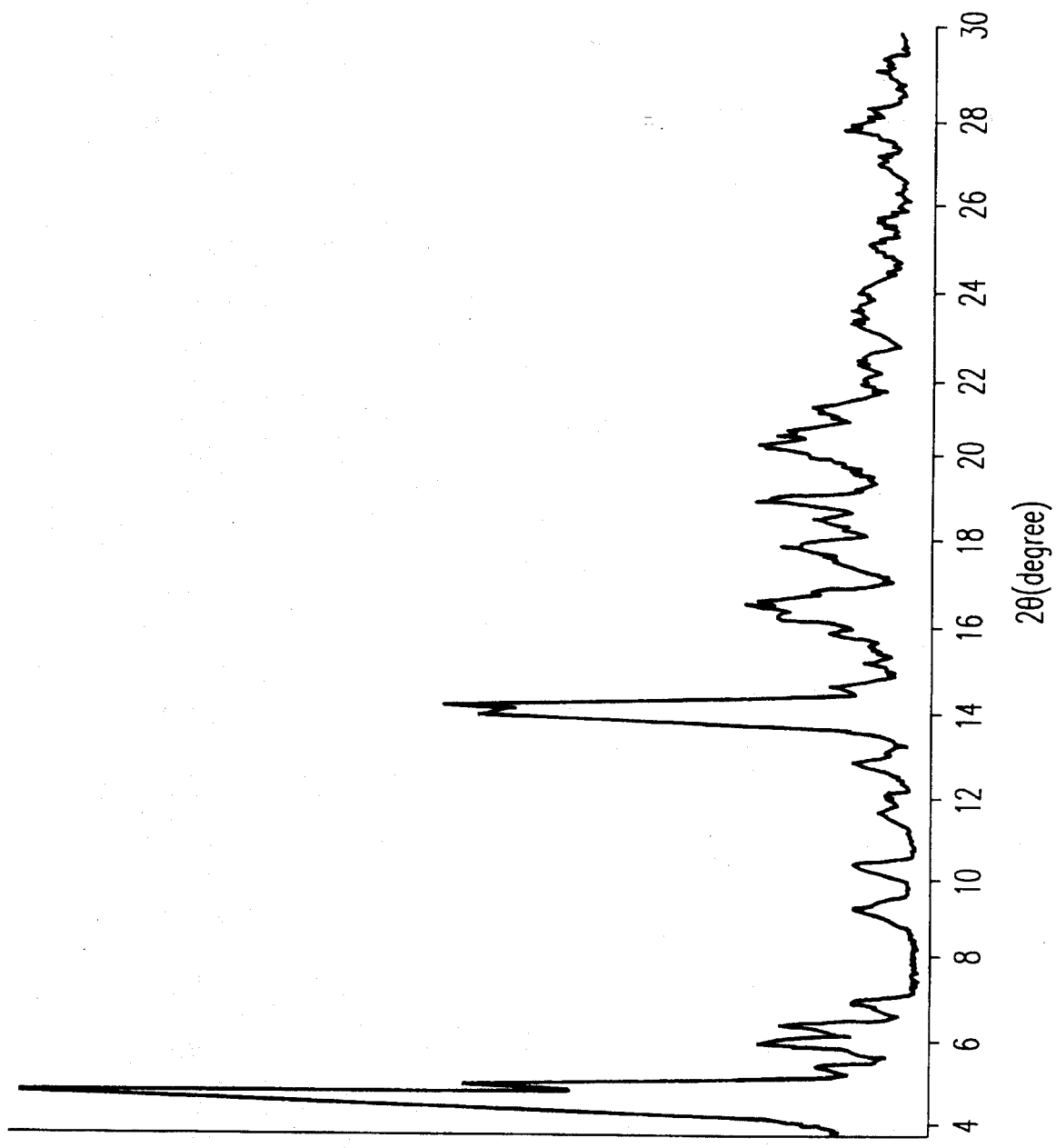
FIG. 1 shows a powder X-ray diffraction pattern of B-type crystals of N-(trans-4-isopropylcyclohexylcarbonyl)-D-phenylalanine.
Figure 3:
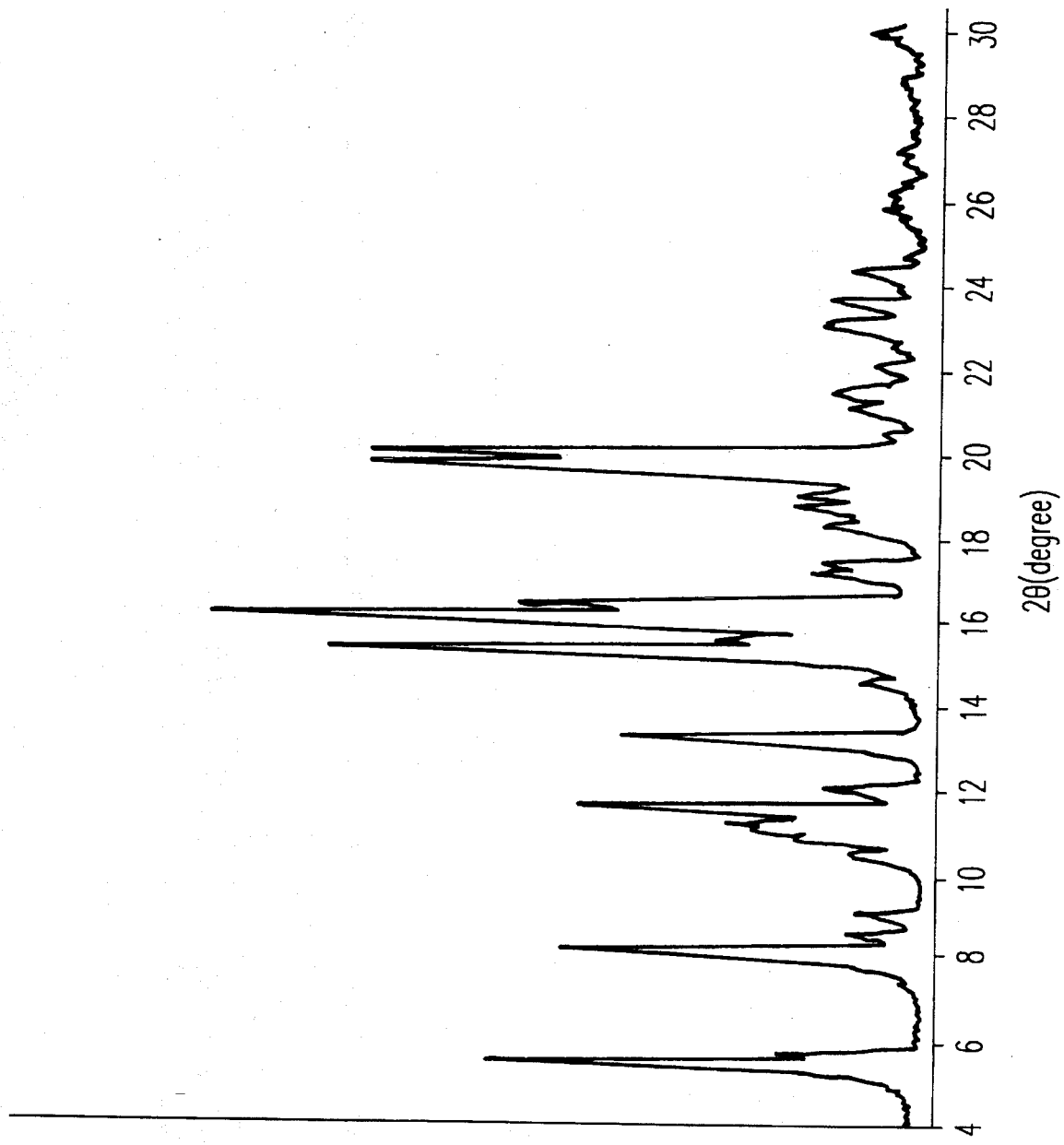
FIG. 3 shows a powder X-ray diffraction pattern of H-type crystals of N-(trans-4-isopropylcyclohexylcarbonyl)-D-phenylalanine.

Examples of powder X-ray diffraction patterns of H-type and B-type crystals may be found at FIGS. 3 and 1 respectively. The diffraction pattern of the H-type crystals shows maxima at 2θ values of 8.1, 13.1, 19.6 and 19.9° where 2θ is the angle between the primary beam projection and the diffracted beam. There are no reflections at these 2θ values in the diffraction pattern of the B-type crystals. The diffraction pattern of H-type crystals also displays strong reflections at 2θ values between about 15° and 17° while the B-type crystals give only weak reflections in this range of 2θ. H-type crystals of the present invention preferably display a powder X-ray diffraction pattern substantially the same as that shown in FIG. 3.

Table 1 below sets out the principal reflections in the powder pattern of H-type crystals in terms of 2θ values and intensity. The data were obtained using a Philips PW1700 powder diffractometer and a scan speed of 0.05°/sec.

TABLE 1

| degree | intensity | degree | intensity | degree | intensity |
|--------|-----------|--------|-----------|--------|-----------|
| 5.5    | S         | 5.7    | M         | 8.1    | S         |
| 8.5    | W         | 9.0    | W         | 10.4   | W         |
| 11.1   | M         | 11.5   | S         | 12.0   | W         |
| 13.1   | S         | 14.3   | W         | 15.2   | S         |
| 15.4   | M         | 15.9   | S         | 16.2   | S         |
| 17.0   | W         | 17.3   | W         | 18.2   | W         |
| 18.6   | W         | 18.9   | W         | 19.6   | S         |
| 19.9   | S         | 21.1   | W         | 21.5   | W         |
| 22.1   | W         | 23.1   | W         | 23.7   | W         |
| 24.5   | W         | 29.9   | W         |        |           |

S; strong, M; medium, W; weak

Figure 2:
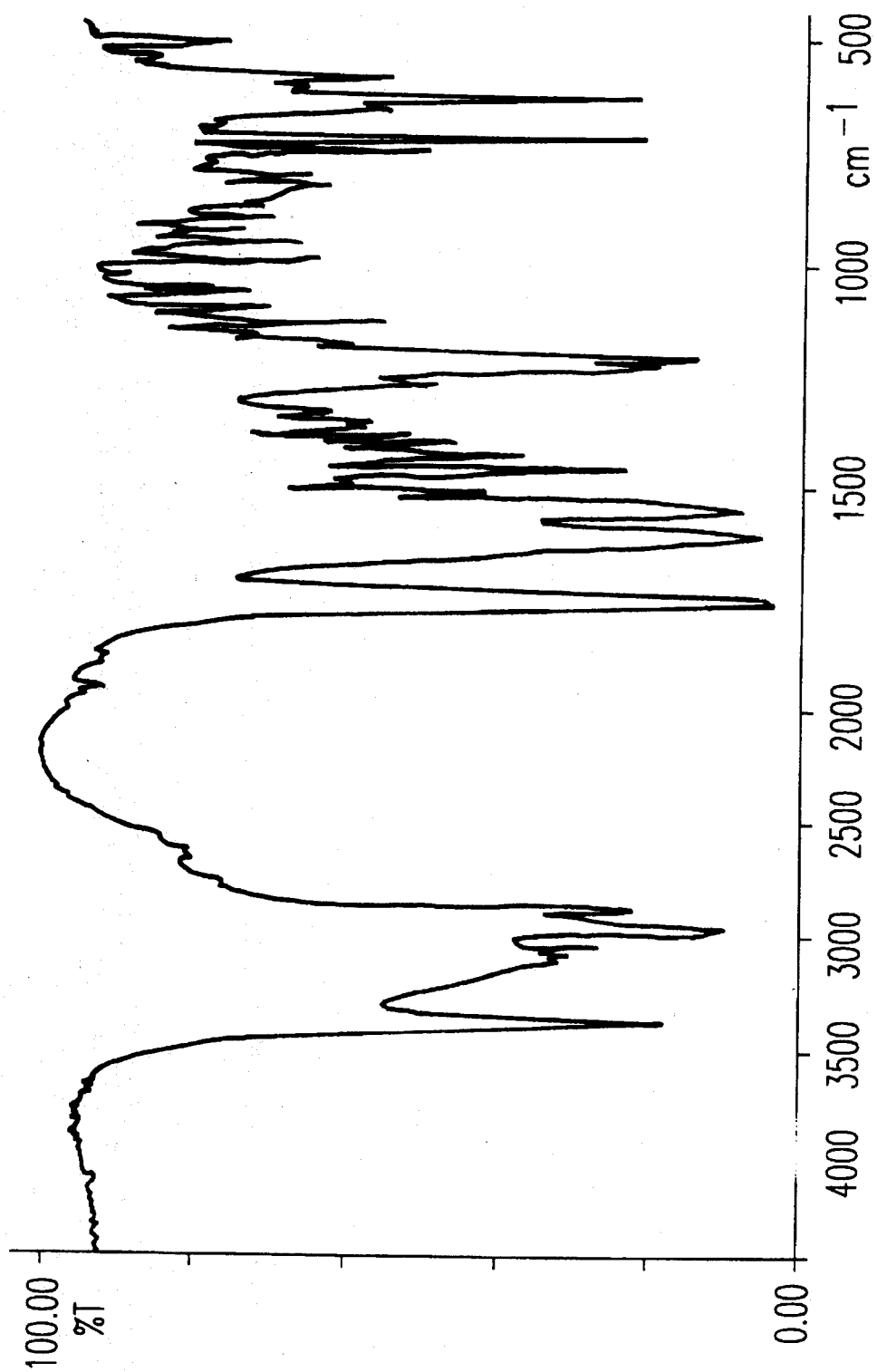
FIG. 2 shows an infra red absorption spectrum of B-type crystals of N-(trans-4-isopropylcyclohexylcarbonyl)-D-phenylalanine.
Figure 4:
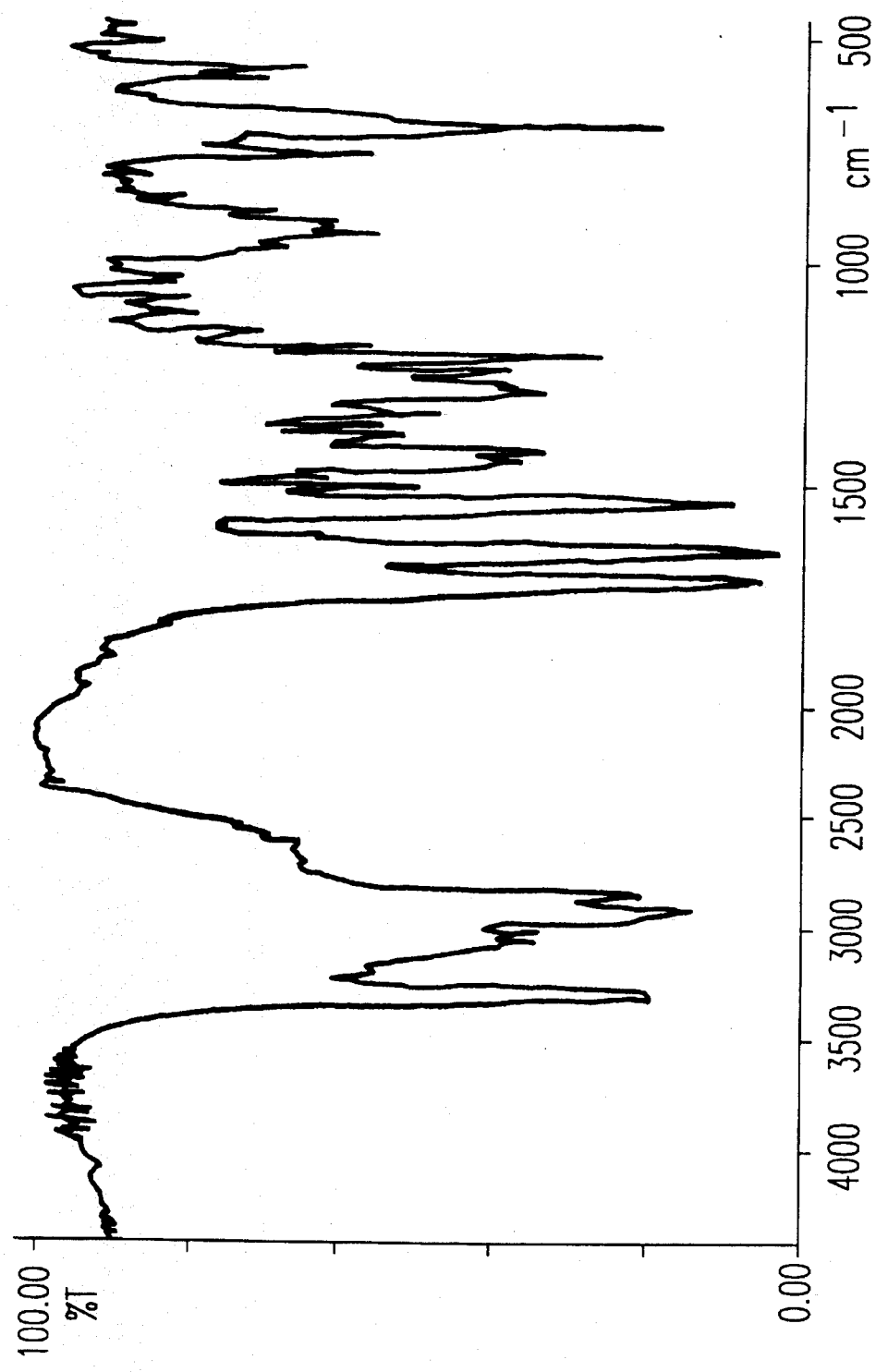
FIG. 4 shows an infra red absorption spectrum of H-type crystals of N-(trans-4-isopropylcyclohexylcarbonyl)-D-phenylalanine.

An example of an infra red adsorption spectrum of H-type crystals, obtained by the KBr method is shown at FIG. 4, and that of B-type crystals as obtained by the same method is shown at FIG. 2. The infra red spectrum of the H-type crystals is characterized by absorptions at around 1714 $cm^{-1}$ 1649 $cm^{-1}$, 1542 $cm^{-1}$ and 1214 $cm^{-1}$, which absorptions are not present in the spectrum of the B-type crystals. H-type crystals of the present invention -preferably display an infra red spectrum substantially the same as that shown in FIG. 4.

The inventors carried out elementary analysis of both H-type and B type crystals and the results are shown in Table 2. These confirm that the two crystal types have the same chemical composition ($C_{19}H_{27}NO_3$)

TABLE 2

|                               | C     | H    | N    |
|-------------------------------|-------|------|------|
| Calculated data (H- or B-type) (%) | 71.89 | 8.57 | 4.41 |
| Measured data (H-type) (%)    | 71.98 | 8.69 | 4.33 |
| Measured data (B-type) (%)    | 71.82 | 8.66 | 4.27 |

H-type crystals are preferably substantially stable to grinding. Stability to grinding may be assessed by measurement of an appropriate physical property before and after grinding. Where the physical property remains substantially unchanged substantial stability to grinding is indicated. Suitable physical properties for measurement include melting point, differential scanning calorimeter trace X-ray diffraction pattern and infra red absorption spectrum, particularly the X-ray diffraction pattern.

As mentioned above the first aspect of the invention provides a method for the production of crystals of N-(trans-4-isopropylcyclohexylcarbonyl)-D-phenylalanine the method comprising treating N-trans-4-isopropylcyclohexylcarbonyl)-D-phenylalanine with a solvent at a temperature of at least 10° C. and forming crystals in the solvent at a temperature of at least 10° C.

In one embodiment -4-isopropylcyclohexylcarbonyl)-D-phenylalanine is dissolved in the solvent at a temperature of at least 10° C. The solution may be produced by dissolving in a solvent any one or more of amorphous N-(trans-4-isopropylcyclohexylcarbonyl)-D-phenylalanine, B-type crystals of the compound, and solvates of the compound such as hydrates, methanolates, ethanolates, isopropanolates and acetonitrilates.

Crystals may then be formed by crystallization from solution, the crystallization from solution taking place at a temperature between 10° C. and the boiling point of the solvent. The crystals thus formed generally comprise enhanced amounts of H-type crystals relative to the starting N-(trans-4-isopropylcyclohexylcarbonyl)-D-phenylalanine. Preferably, the product is predominantly H-type crystals.

The dissolution and crystallization at a temperature of at least 10° C. may be carried out in several ways as will be apparent to those of skill in the art. For instance, N-(trans-4-isopropylcyclohexylcarbonyl)-D-phenylalanine may be dissolved in a solvent, or mixture of solvents in which it is readily soluble at elevated temperatures but in which it is only sparingly soluble at lower temperatures (which are still at least 10° C.). Dissolution at elevated temperature is, in this case, followed by cooling during which the desired H-type crystals crystallize out of solution. Solvents which are suitable for use in this way include esters, such as methyl acetate and ethyl acetate, toluene and acetonitrile. Mixed solvents comprising a good solvent in which N-(trans-4-isopropylcyclohexylcarbonyl)-D-phenylalanine is readily soluble, as a first solvent, preferably, in amounts of at least 1 weight % at 30° C., and a poor solvent in which it is more sparingly soluble, as a second solvent, preferably, in amounts of not more than 0.01% at 30° C., may also be employed provided that crystallization from the mixture at a temperature of at least 10° C. is possible using the selected solvent mixture. A preferred solvent mixture is a solution which is a mixture of a first solvent selected from the group consisting of acetone, ethanol and isopropanol with water as a second solvent.

The concentration of the first solvent is preferably from 30 to 60 vol % of the solvent mixture. The temperature of the solution is preferably 15° to 50° C.

An alternative way of achieving crystallization from solution at a temperature of 10° C. is to utilize the difference in solubility of the crystals in different solvents. For example, N-(trans-4-isopropylcyclohexylcarbonyl)-D-phenylalanine may be dissolved in a good solvent in which it is highly soluble, as a first solvent, such as one in which it is soluble in amounts of at least 1 weight % at 30° C. and the solution subsequently mixed with a poor solvent in which it is more sparingly soluble, as a second solvent, such as one in which it is soluble in amounts of not more than 0.01% at 30° C. Thus, the solution of N-(trans-4-isopropylcyclohexylcarbonyl)-D-phenylalanine in the good solvent might be added to the poor solvent, while maintaining a temperature in excess of 10° C., or the poor solvent might be added to the solution of N-(trans-4-isopropylcyclohexylcarbonyl)-D-phenylalanine in the good solvent, again while maintaining a temperature in excess of 10° C. Examples of good solvents include lower alcohols, such as methanol, ethanol and isopropanol, as well as acetone, tetrahydrofuran and dioxane. Examples of poor solvents are water, hexane and diethyl ether. Preferably, the first solvent is selected from the group consisting of acetone, ethanol and isopropanol, and the second solvent is water. The temperature of the solution if preferably from 15° to 50° C.

Whichever of the two alternative crystallization methods is employed it is important that the crystallization temperature be at least 10° C. up to the boiling point of the solvent. If the temperature employed is lower than 10° C. it is not possible to obtain good yields of H-type crystals. Preferably, crystallization is effected at a temperature in the range of 10° to 60° C., more preferably at least 15° C., especially preferably from 20° to 60° C. and most preferably from 15° to 50° C.

Crystals which have come out of solution are preferably separated from the solvent e.g., by filtration or centrifuging and are desirably then dried for example at a temperature in the range of from 20° C. to 100° C.

In an alternative embodiment of the first aspect of the invention solid N-(trans-4-isopropylcyclohexylcarbonyl)-D-phenylalanine is suspended at a temperature of at least 10° C. in a solvent in which it is incompletely soluble, preferably only sparingly soluble, at that temperature. A suspension results in which particles of solid are dispersed, and remain incompletely dissolved in the solvent. Preferably the solids are maintained in a state of suspension by agitation e.g., by shaking or stirring. The suspension is kept at a temperature of 10° C. or higher thereby to effect a transformation of the staring solids into product crystals.

The solid N-(trans-4-isopropylcyclohexylcarbonyl)-D-phenylalanine suspended in suitable solvent may be of any type, such as amorphous, or in the form of B-type crystals and may be a solvate, e.g. hydrate, methanolate, ethanolate, isopropanolate or acetonitrilate. The amorphous powder may be derived by drying a solvate. Preferably, the suspension is maintained at a temperature of at least 10° C. for sufficiently long that the product crystals contain enhanced amounts of H-type crystals relative to the starting N-(trans-4-isopropylcyclohexylcarbonyl)-D-phenylalanine.

Solvents suitable for use in this embodiment of the invention include water, esters such as methyl acetate and ethyl acetate, as well as toluene. Good solvents in which N-(trans-4-isopropylcyclohexylcarbonyl)-D-phenylalanine is more readily soluble for example in amounts of at least 1% by weight at 30° C., such as lower alcohols e.g. methanol, ethanol and isopropanol, as well as acetone, acetonitrile, tetrahydrofuran and dioxane may also be used provided they are used in combination with a solvent in which N-(trans-4-isopropylcyclohexylcarbonyl)-D-phenylalanine is only poorly soluble for example in amounts of 0.01 weight % or less, e.g. water, hexane or diethyl ether. Where a mixed solvent is employed the concentration of good solvent is generally 70% by volume or less. Where it exceeds 70% by volume the solubility of N-(trans-4-isopropylcyclohexylcarbonyl)-D-phenylalanine in the mixed solvent would be so high that the yield of desired H-type crystals would be disadvantageously low. Generally, the use of a mixed solvent gives rise to a favorable results. A solvent which is a mixture of a first good solvent selected from the group consisting of acetone, ethanol and isopropanol with water as a second solvent is effective. A concentration of the good solvent in the solvent mixture of from 25 to 50 mol % of the solvent mixture is preferred. The temperature of the suspension is preferably at 15° to 50° C. Preferably, the amount of N-(trans-4-isopropylcyclohexylcarbonyl)-D-phenylalanine dispersed in the solvent is from 0.5% to 30% by weight of the resulting suspension. If it is more than 30% by weight then the slurry properties of the suspension are poor and it will be difficult to agitate. On the other hand, it is not efficient in terms of the volume of solvent required to use less than 0.5% by weight. Preferably the suspension includes from 1% to 15% by weight.

The suspension is maintained at a temperature from 10° C. to the boiling point of the solvent, in general above 15° C. as from 20° C. to 70° C. or from 15° C. to 50° C. Temperatures below 10° C. do not facilitate transformation of the solids to H-type crystals. The time for which the suspension is left before H-type crystals may be collected from it varies depending on the nature of the solvent(s) used, the temperature and other factors, such as the quantity of solids in suspension and the size of the solid particles.

Generally, however, it may be in the range of from 10 minutes to 48 hours. By adding H-type crystals of N-(trans-4-isopropylcyclohexylcarbonyl)-D-phenylalanine to the dispersion as seed crystals, the time required to form H-type crystals may be shortened. The end point in formation of H-type crystals can be determined by sampling crystals from the suspension, for example by filtration during the course of the conversion followed by measuring the powder X-ray diffraction pattern or infra red absorption spectrum of the crystals.

It is preferable to allow the crystals to remain in suspension for a period long enough to convert them to the H-type, such as a period exceeding 12 hours, or to carry out crystallization slowly, such as for a period exceeding 6 hours, at the industrial scale.

The H-type crystals as obtained in the manner mentioned above can be separated from suspension by filtration or centrifugation. In isolating them, cooling may be effected, if desired. In that case, the cooling temperature is preferably no lower than 10° C. The isolated crystals are dried, for example at a temperature in the range of from 20° to 120° C.

According to another aspect of the invention there is provided a pharmaceutical composition comprising crystals as obtainable by the method of the first aspect, in particular H-type crystals, and a pharmaceutically acceptable excipient, diluent or carrier.

According to a still further aspect of the invention there is provided a method of manufacture of a pharmaceutical composition comprising mixing an effective amount of crystals as obtainable by the method of the first aspect of the invention, in particular H-type crystals and a pharmaceutically acceptable excipient diluent or carrier.

According to a still further aspect of the invention there is provided a method for treatment of a human or other mammal to depress its blood glucose level comprising administering an effective amount of N-(trans-4-isopropylcyclohexylcarbonyl)-D-phenylalanine crystals as obtainable by the methods of the present invention, in particular B-type crystals.

EXAMPLES

Embodiments of the invention are illustrated below by way of example only.

N-(trans-4-isopropylcyclohexylcarbonyl)-D-phenylalanine for use in the following examples was obtained by the method described in Example 3 of Japanese patent application laid open no. 63-54321. The product contained crystals of B-type.

(A) H-Type Crystals by Crystallization from Solution

Example A1

20 ml of an acetone solution of 5 g of N-(trans-4-isopropylcyclohexylcarbonyl)-D-phenylalanine were added dropwise to a stirred mixture of acetone (40 ml) and water (60 ml) at 25° C. After cooling to 10° C., the precipitated crystals were filtered and dried at 90° C. at reduced pressure overnight. 4.5 g of dry crystals were obtained. The crystals had a melting point of 138° to 141° C. The powder X-ray diffraction pattern and the infra-red absorption spectrum were measured and the crystals were thus identified as H-type.

Example A2

N-(trans-4-isopropylcyclohexylcarbonyl)-D-phenylalanine (4 g) was dissolved in a mixture of ethanol (50 ml) and water (50 ml) at 45° C. The solution was cooled with stirring. H-type crystals of N-(trans-4-isopropylcyclohexylcarbonyl)-D-phenylalanine (0.1 g) prepared in Example A1 were added at a temperature of 37° C. and the solution was cooled further to 25° C. The crystals were filtered and dried at 60° C. overnight and at reduced pressure. 2.5 g of dry crystals were obtained. The crystals had a melting-point of 138° to 141° C. The powder X-ray diffraction pattern and the infra-red absorption spectrum enabled the crystals to be identified as H-type.

Example A3

N-(trans-4-isopropylcyclohexylcarbonyl)-D-phenylalanine (0.5 g) was dissolved in acetonitrile at 45° C. and the solution was cooled to 25° C. The precipitated crystals were filtered and dried at 90° C. under reduced pressure. 0.48 g of dry crystals were obtained. The crystals had a melting point of 138° to 141° C. Their powder X-ray diffraction pattern and infra red absorption spectrum were consistent with their being H-type crystals.

Comparative Example A1

The procedure of Example A1 was followed but cooling to 5° C. was employed. 4.6 g of dry crystals were obtained. The crystals had a melting point of 128° to 131° C. The powder X-ray diffraction pattern and the infra-red absorption spectrum of the crystals were measured and the crystals were identified as B-type.

Comparative Example A2

N-(trans-4-isopropylcyclohexylcarbonyl)-D-phenylalanine (5 g) was dissolved in a mixture of ethanol (60 ml) and water (40 ml) at 30° C. The solution was cooled to 5° C. with stirring. The precipitated crystals were filtered and dried at 90° C. under reduced pressure, and overnight. 3.3 g of dried crystals were obtained. The crystals had a melting point of 128 to 131° C. and their powder X-ray diffraction pattern and infra-red absorption spectrum indicated that they were of the B-type.

Comparative Example A3

N-(trans-4-isopropylcyclohexylcarbonyl)-D-phenylalanine (5 g) was dissolved in a mixture of methanol (70 ml) and water (30 ml) at 40° C. The solution was cooled to 5° C. with stirring. The precipitated crystals were filtered and dried at 90° C. under reduced pressure overnight. 3.5 g of dry crystals were obtained. Once again, the crystals had a melting point of 128° to 131° C. The powder X-ray diffraction pattern and the infra-red absorption spectrum were consistent with the crystals being B-type.

(B) H-Type Crystals from Suspension

Example B1

B-type crystals of N-(trans-4-isopropylcyclohexylcarbonyl)-D-phenylalanine (3 g) were dispersed in 300 ml of water and stirred at 30° C. for 1 day. The crystals were filtered and dried at 90° C. under reduced pressure overnight. 2.9 g of dry crystals were obtained. The powder X-ray diffraction pattern and the infra-red absorption spectrum were recorded and indicated that the crystals were of H-type.

Example B2

B-type crystals of N-(trans-4-isopropylcyclohexylcarbonyl)-D-phenylalanine (4 g) were dispersed in a mixture of acetone (40 ml) and water (60 ml) and stirred at 20° C. overnight. The crystals were subsequently filtered off and dried at 90° C. under reduced pressure overnight. 3.6 g of dry crystals were obtained. Powder X-ray diffraction and infra red absorption spectroscopy indicated that the product crystals were of H-type.

Example B3

Hydrate of N-(trans-4-isopropylcyclohexylcarbonyl)-D-phenylalanine for use in this example was prepared as follows. 20 g of B-type crystals of N-(trans-4-isopropylcyclohexylcarbonyl)-D-phenylalanine were dissolved in a mixture of ethanol (300 ml) and water (200 ml) at 30° C. The solution was cooled to 5° C. with stirring. The precipitated crystals were filtered off and dried at 40° C. under reduced pressure for 2 hours. 13.9 g of dried crystals resulted.

4.2 g of the hydrate was dispersed in a mixture of ethanol (30 ml) and water (70 ml) and stirred at 45° C. overnight. The crystals were filtered off and dried at 90° C. under reduced pressure overnight. 3.8 g of dried crystals were obtained. These were found to be of the H-type by powder X-ray diffraction and infra-red spectroscopy.

Example B4

4.2 g of the hydrate of N-(trans-4-isopropylcyclohexylcarbonyl)-D-phenylalanine prepared as in example B3 was dispersed in a mixture of ethanol (30 ml) and water (70 ml). 40 mg of H-type crystals were added and the dispersion was stirred at 45° C. for 1 hour.

The crystals were filtered off and dried at 90° C. under reduced pressure overnight. 3.9 g of dry crystals were obtained. These were found to be of the H-type by X-ray diffraction and infra red absorption spectroscopy.

Example B5

B-type crystals of N-(trans-4-isopropylcyclohexylcarbonyl)-D-phenylalanine (5 g) were dispersed in a mixture of isopropanol (25 ml) and water (75 ml) and stirred at 50° C. for 10 hours. The resulting crystals were filtered off and dried at 90° C. under reduced pressure overnight. 4.4 g of dry crystals were obtained. These were found to be of the H-type by X-ray diffraction and infra red spectroscopy.

Comparative Example B1

4 g of B-type crystals of N-(trans-4-isopropylcyclohexylcarbonyl)-D-phenylalanine were dispersed in a mixture of acetone (40 ml) and water (60 ml) and stirred at 5° C. overnight. The crystals were filtered off and dried at 90° under reduced pressure overnight. 3.6 g of dry crystals were obtained. The powder X-ray diffraction pattern and the infra red absorption spectrum were measured and the crystals were found to be of B-type.

(C) Stability to Grinding

In order to demonstrate the stability of H-type crystals to grinding the following experiment was carried out.

H-type crystals of N-(trans-4-isopropylcyclohexylcarbonyl)-D-phenylalanine and the previously known B-type crystals were each mechanically-ground in a grinder, and the X-ray diffraction pattern of each powder was measured and compared with the spectrum before grinding. No change was observed in the H-type crystals before and after grinding but changes were observed in the diffraction pattern of the B-type crystals.

Figure 5A:
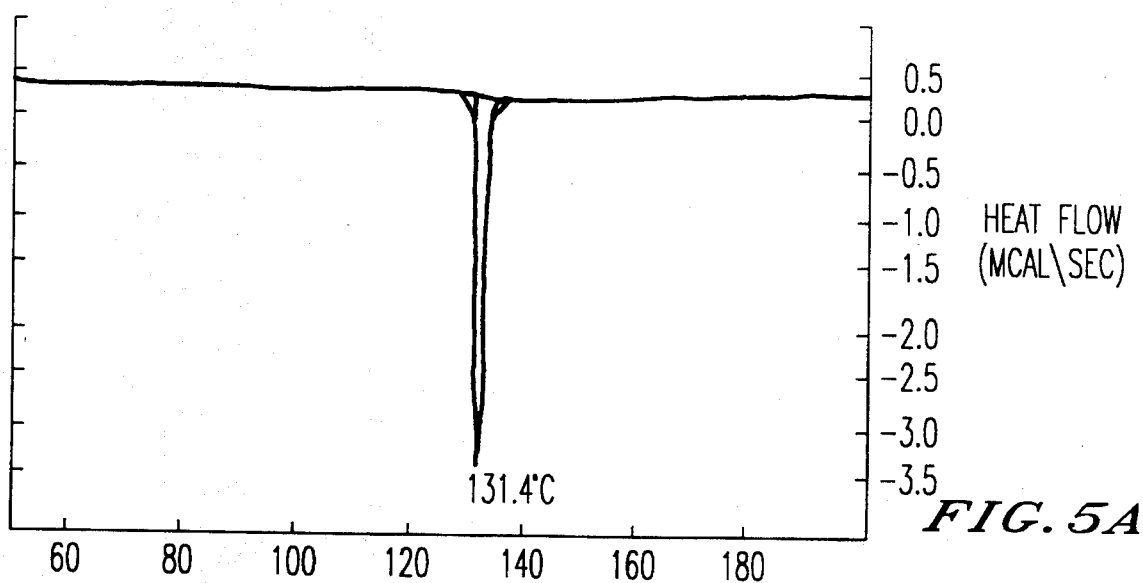
FIG. 5 shows differential scanning calorimeter (DSC) traces of: B-type crystals before grinding (FIG. 5a); H-type crystals before grinding (FIG. 5b); B-type crystals after grinding (FIG. 5c).
Figure 5B:
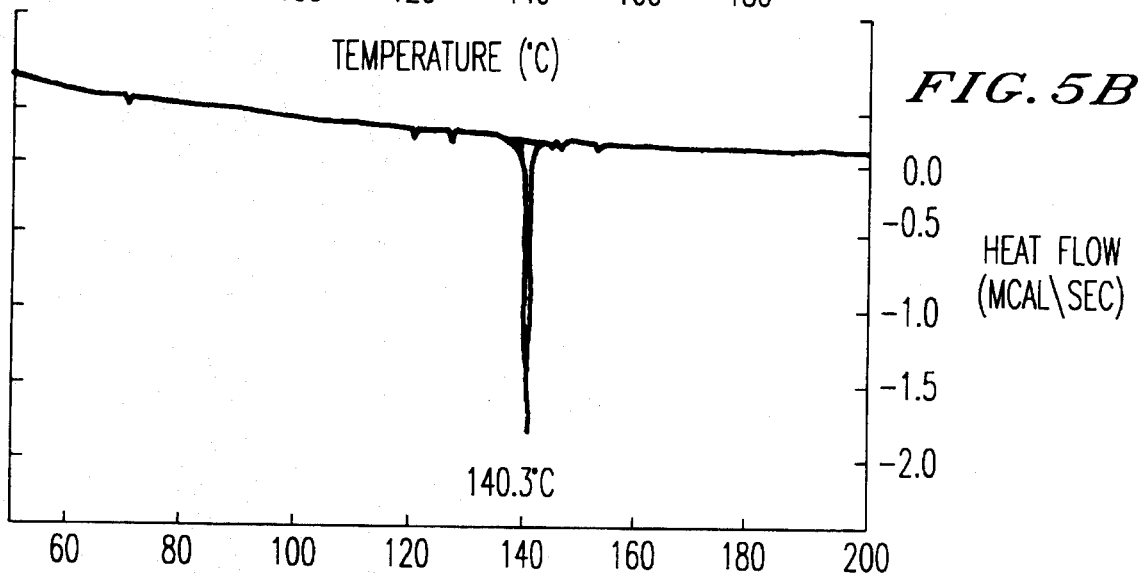
Figure 5C:
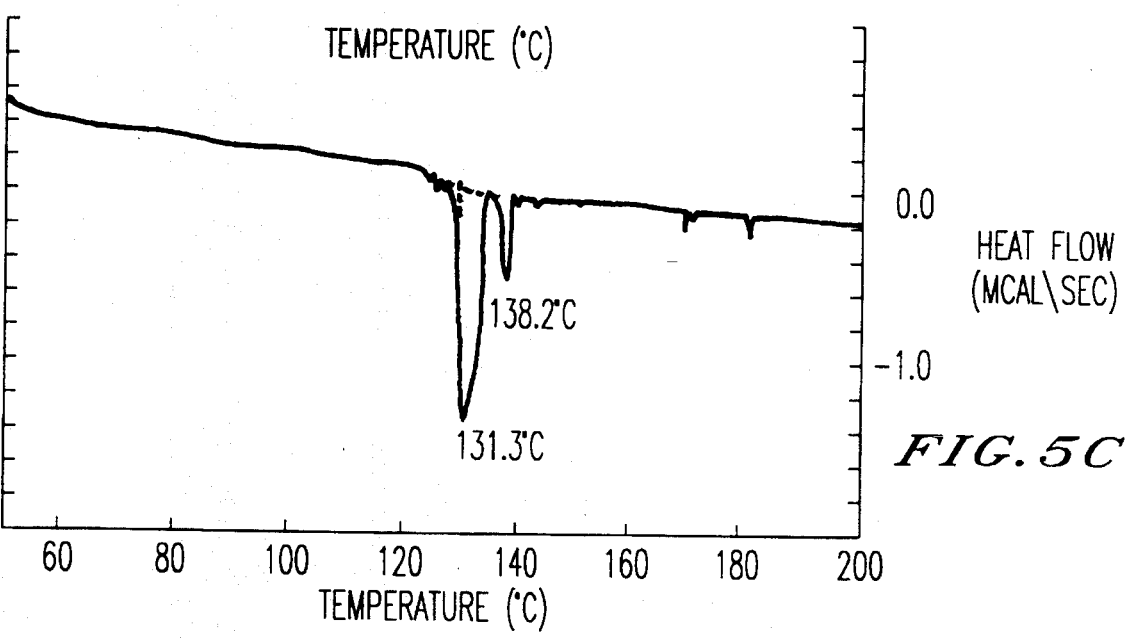

Similarly, the differential scanning calorimeter (DSC) trace for each of the H-type, and B-type crystals was measured before and after grinding. FIG. 5a shows the DSC trace of B-type crystals before grinding. The crystals show a sharp melting point at around 130° C. The DSC trace of H-type crystals before grinding is shown in FIG. 5b. These crystals also demonstrated a sharp melting point at around 140° C. The DSC trace of the H-type crystals was unchanged by grinding. By contrast, the trace shown in FIG. 5c for B-type crystals after grinding differs from the trace obtained before grinding and new troughs are visible in the trace.

Additional Examples of the preparation of H-type crystals are as follows.

Example D1

44 g of hydrate of N-(trans-4-isopropylcyclohexylcarbonyl)-D-phenylalanine, containing 18 g of water, were dissolved in ethanol (292 ml). The solution was added dropwise to a suspension of H-type crystals of N-(trans-4-isopropylcyclohexylcarbonyl)-D-phenylalanine (0.4 g), prepared in Example A1, in a mixture of water (340 ml) and ethanol (88 ml) at 42° C. in three hours, simultaneously with addition of water (350 ml). The resulting mixture was stirred at the same temperature overnight, then the precipitated crystals were filtered and dried under reduced pressure to give 23 g of dry crystals which had a melting point of 139° C. The crystals were identified as H-type by powder X-ray diffraction pattern and infra-red absorption spectrum.

Example D2

46 g of hydrate of N-(trans-4-isopropylcyclohexylcarbonyl)-D-phenylalanine, containing 18 g of water, were dissolved in ethanol (307 ml). The solution was added dropwise to a suspension of H-type crystals of N-(trans-4-isopropylcyclohexylcarbonyl)-D-phenylalanine (0.4 g), prepared in Example A1, in a mixture of water (429 ml) and ethanol (98 ml) at 42° C. in 40 minutes. Water was added in 5 hours, and then the resulting mixture was stirred at the same temperature overnight. The precipitated crystals filtered and dried under reduced pressure to give 25 g of dry crystals which had a melting point of 138° C. The crystals were identified as H-type by powder X-ray diffraction pattern and infra-red absorption spectrum.

Example D3

48 g of hydrate of N-(trans-4-isopropylcyclohexylcarbonyl)-D-phenylalanine, contaning 19 g of water, were dissolved in ethanol (228 ml). The Solution was added to a mixture of water (323 ml) and ethanol (118 ml) at 45° C. After cooling to 40° C, H-type crystals of N-(trans-4-isopropylcyclohexylcarbonyl)-D-phenylalanine (0.45 g), prepared in Example A1, and then water (317 ml) were added in 2.5 hours, and the resulting mixture was stirred at the same temperature overnight. The precipitated crystals filtered and dried under reduced pressure to give 27 g of dry crystals which had a melting point of 139° C. The crystals were identified as H-type by powder X-ray diffraction pattern and infra-red absorption spectrum.

What is claimed as new and is desired to be secured by Letters Patent of the United States is:

1. Crystals of N-(trans-4-isopropylcyclohexylcarbonyl)-D-phenylalanine having at least one of the following properties:

(a) a melting point in the range of 136°–142° C.

(b) a powder X-ray diffraction pattern with reflection maxima at 2θ of about 8.1°, 13.1°, 19.6° and 19.9°;

(c) an infra red absorption spectrum with absorption bands in the region of 1714, 1649, 1542 and 1214 cm$^{-1}$.

2. Crystals of N-(trans-4-isopropylcyclohexylcarbonyl)-D-phenylalanine according to claim 1 having all three of the properties (a), (b) and (c).

3. Crystals of N-(trans-4-isopropylcyclohexylcarbonyl)-D-phenylalanine having at least one of an X-ray powder diffraction pattern as shown in FIG. 3 and an infra red spectrum as shown in FIG. 4.

4. Crystals according to any one of claims 1 and 3 in the substantial absence of solvent.

5. A pharmaceutical composition comprising an effective amount of crystals according to claim 1 and a pharmaceutically acceptable excipient, diluent or carrier.

6. A method for the production of crystals of N-(trans-4-isopropylcyclohexylcarbonyl)-D-phenylalanine having at least one the following properties:

(a) a melting point in the range of 136°–142° C.;

(b) a powder X-ray diffraction pattern with reflection maxima at 2θ of about 8.1°, 13.1°, 19.6° and 19.9°;

(c) an infra red absorption spectrum with absorption bands in the region of 1714, 1649, 1542 and 1214 cm$^{-1}$, comprising dissolving or suspending an N-(trans-4-isopropylcyclohexylcarbonyl)-D-phenylalanine not possessing any of said properties in a solvent in which it is completely or incompletely soluble at a temperature of at least 15° C. and up to the boiling point of the solvent and permitting said crystals to crystallize from or form in said solvent at a temperature of 15° C. of in excess thereof.

7. The method according to claim 6, wherein the N-(trans-4-isopropylcyclohexylcarbonyl)-D-phenylalanine is dissolved in a solvent in which it is soluble at a temperature greater than 15° C. to form a solution and from which it may be precipitated by cooling to a lower temperature of 15° C. or higher and crystals are then crystallized from the solution at a temperature of 15° C. or in excess thereof by reducing the temperature of the solution to a temperature of 15° C. or in excess thereof.

8. The method according to claim 6, wherein the N-(trans-4-isopropylcyclohexylcarbonyl)-D-phenylalanine is dissolved in a first solvent from which it may be precipitated by addition of a second solvent and the crystallization from solution in the first solvent is effected at a temperature of 15° C. or in excess thereof by adding to the solution a second solvent miscible with the first solvent selected such that the solubility of said N-(trans-4-isopropylcyclohexylcarbonyl)-D-phenylalanine in the mixture of the first solvents and second solvent is less than in the first solvent, the solubility being reduced to an extent such that crystals crystallize from the solvent mixture at a temperature in excess of 15° C.

9. The method according to claim 6, wherein the N-(trans-4-isopropylcyclohexylcarbonyl)-D-phenylalanine is combined at a temperature of at least 15° C. with a solvent in which it is incompletely soluble at that temperature to form a suspension of solid N-(trans-4-isopropylcyclohexylcarbonyl)-D-phenylalanine, and said suspension is maintained at a temperature of at least 15° C., thereby to form said crystals from said solids.

10. The method according to claim 6 further comprising separating said crystals from the solvent at a temperature in excess of 15° C.

11. The method according to claim 7, wherein the solvent is a mixture of a first solvent selected from the group consisting of acetone, ethanol and isopropanol with water as a second solvent.

12. The method according to claim 11, wherein the concentration of the first solvent is from 30 to 60 vol % of the solvent mixture.

13. The method according to claim 11, wherein the temperature of the solution is from 15° to 50° C.

14. The method according to claim 8, wherein the first solvent is selected from the group consisting of acetone, ethanol and isopropanol, and the second solvent is water.

15. The method according to claim 14, wherein the temperature of solution is from 15° to 50° C.

16. The method according to claim 9, wherein the solvent is a mixture of a first solvent selected from the group consisting of acetone, ethanol and isopropanol with water as a second solvent.

17. The method according to claim 16, wherein the concentration of first solvent in the solvent mixture is from 25 to 50 vol % of the solvent mixture.

18. The method according to claim 9, wherein the solvent is water.

19. The method according to claim 16, wherein the temperature of the suspension is from 15° to 50° C.

* * * * *

UNITED STATES PATENT AND TRADEMARK OFFICE
CERTIFICATE OF CORRECTION

PATENT NO. : 5,463,116
DATED : October 31, 1995
INVENTOR(S) : Michito SUMIKAWA et al.

It is certified that error appears in the above-indentified patent and that said Letters Patent is hereby corrected as shown below:

On the title page, item [54] & Column 1, the title should read:

--CRYSTALS OF N-(TRANS-4-ISOPROPYLCYCLOHEXYLCARBONYL)-D-PHENYLALANINE AND METHODS FOR PREPARING THEM--

Signed and Sealed this

Fifth Day of March, 1996

Attest:

BRUCE LEHMAN

*Attesting Officer*   *Commissioner of Patents and Trademarks*